United States Patent
Steffen et al.

(10) Patent No.: US 7,326,747 B2
(45) Date of Patent: Feb. 5, 2008

(54) INTERNAL WETTING AGENT FOR USE IN MANUFACTURE OF POLYMERIC FILMS AND FABRICS FOR DISPOSABLE ABSORBENT ARTICLES

(75) Inventors: John Steffen, Sugar Hill, GA (US); Brian Smith, Gainesville, GA (US)

(73) Assignee: Polymer Group, Inc., Charlotte, NC (US)

( * ) Notice: Subject to any disclaimer, the term of this patent is extended or adjusted under 35 U.S.C. 154(b) by 496 days.

(21) Appl. No.: 10/001,363

(22) Filed: Oct. 25, 2001

(65) Prior Publication Data

US 2002/0115970 A1     Aug. 22, 2002

Related U.S. Application Data

(60) Provisional application No. 60/244,458, filed on Oct. 31, 2000.

(51) Int. Cl.
*C08K 5/103*     (2006.01)
*C08K 3/22*      (2006.01)
*C08L 23/04*     (2006.01)

(52) U.S. Cl. .................. 524/317; 524/313; 524/310; 524/497; 524/585; 524/586; 524/570

(58) Field of Classification Search .......... 524/585, 524/497, 564, 230, 586, 317, 313, 310, 570
See application file for complete search history.

(56) References Cited

U.S. PATENT DOCUMENTS

| | | | | |
|---|---|---|---|---|
| 3,607,341 A | * | 9/1971 | Goins et al. | 442/374 |
| 3,668,172 A | * | 6/1972 | Jones et al. | 524/238 |
| 3,839,078 A | | 10/1974 | Birchall et al. | |
| 4,029,101 A | | 6/1977 | Chesky et al. | |
| 4,036,675 A | | 7/1977 | Amberg et al. | |
| 4,087,505 A | * | 5/1978 | Sugimoto et al. | 264/564 |
| 4,184,498 A | | 1/1980 | Franco | |
| 4,195,634 A | | 4/1980 | DiSalvo et al. | |
| 4,222,913 A | * | 9/1980 | Cooper | 524/310 |
| 4,329,309 A | | 5/1982 | Kelly | |
| 4,381,326 A | | 4/1983 | Kelly | |

(Continued)

FOREIGN PATENT DOCUMENTS

JP     8-34882     *   2/1996

OTHER PUBLICATIONS

JP 8-34882 (abstract and translation in English), Feb. 1996.*

(Continued)

*Primary Examiner*—Vasu Jagannathan
*Assistant Examiner*—Rip A. Lee
(74) *Attorney, Agent, or Firm*—Kilyk & Bowersox, PLLC; Valerie Calloway

(57) ABSTRACT

An improved internal wetting agent is provided for blending with polymeric material, with the formation of apertured films and/or polymeric fibrous webs contemplated. Films and/or nonwoven fabrics of this nature are suited for use in disposable absorbent articles, particularly for the so-called topsheet or facing layer, which contacts the wearer during use. Because polymeric materials from which these types of facing layers are made are typically hydrophobic, the provision of an internal wetting agent facilitates the passage of liquid through the facing layer into an associated absorbent structure.

4 Claims, 1 Drawing Sheet

U.S. PATENT DOCUMENTS

| | | | | |
|---|---|---|---|---|
| 4,490,323 | A | * | 12/1984 | Thomson ..................... 264/211 |
| 4,672,956 | A | | 6/1987 | Potter et al. |
| 4,704,238 | A | * | 11/1987 | Okuyama et al. ............. 264/41 |
| 4,886,513 | A | | 12/1989 | Mason et al. |
| 5,176,751 | A | * | 1/1993 | Findley ...................... 106/502 |
| 5,387,209 | A | | 2/1995 | Yamamoto et al. |
| 5,582,892 | A | | 12/1996 | Anderson |
| 5,643,669 | A | | 7/1997 | Tsuei |
| 5,843,056 | A | | 12/1998 | Good et al. |
| 5,969,026 | A | * | 10/1999 | Mor et al. .................. 524/317 |
| 6,051,618 | A | * | 4/2000 | Tabaksblat et al. ........... 521/60 |
| 6,146,757 | A | | 11/2000 | Mor et al. |
| 6,190,758 | B1 | * | 2/2001 | Stopper ...................... 428/198 |
| 6,198,018 | B1 | | 3/2001 | Curro |
| 6,303,062 | B1 | * | 10/2001 | Aamodt et al. ............. 264/167 |
| 6,395,812 | B1 | * | 5/2002 | Nielsen ...................... 524/317 |
| 6,410,823 | B1 | * | 6/2002 | Daley et al. ................ 604/383 |

OTHER PUBLICATIONS

International Search Report for International Application No. PCT/US01/45582, which corresponds to this application.

International Preliminary Examination Report for International Application No. PCT/US01/45582, *supra*.

International Search Report for International Application No. PCT/US01/45582, which corresponds to this application, Mar. 5, 2002.

International Preliminary Examination Report for International Application No. PCT/US01/45582, *supra*, Jan. 30, 2003.

\* cited by examiner

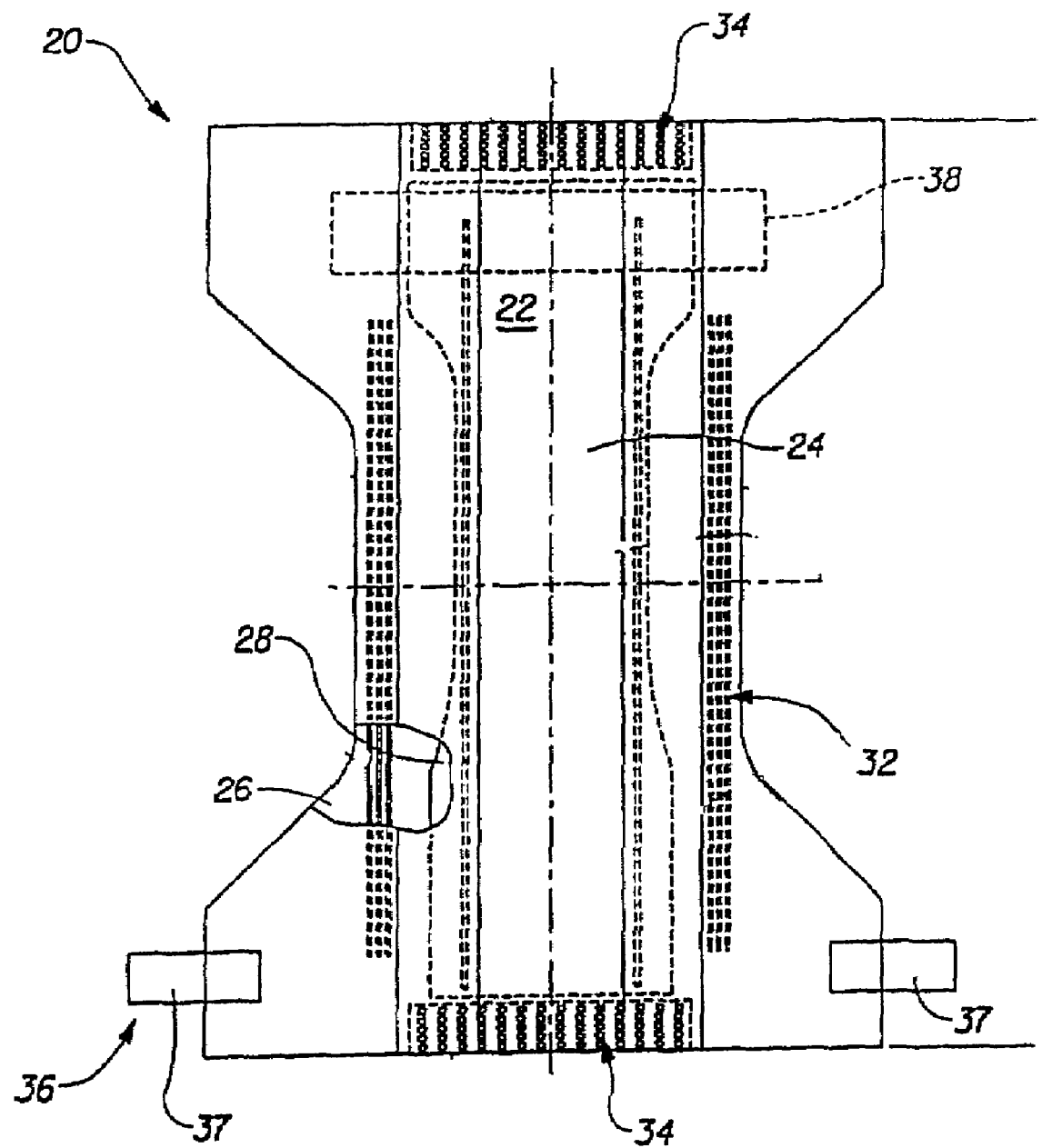
FIG_1

INTERNAL WETTING AGENT FOR USE IN MANUFACTURE OF POLYMERIC FILMS AND FABRICS FOR DISPOSABLE ABSORBENT ARTICLES

TECHNICAL FIELD

The present invention relates generally to wetting agents used in the formation of polymeric compounds used to manufacture apertured films and nonwoven fabrics employed in disposable absorbent articles, and more particularly, to an improved internal wetting agent which, when blended with an associated polymeric material, promotes efficient formation of films and fabrics without unintended holes, discontinuities, or like defects.

BACKGROUND OF THE INVENTION

Disposable absorbent articles, including disposable diapers, sanitary protection products, training pants, and adult incontinent products, typically include a so-called top sheet or facing layer positioned for contact with the user. This component of an absorbent article is foraminous in nature, such as by aperturing of a plastic film, or by virtue of the fibrous nature of a nonwoven fabric, whereby liquid introduced into the article can pass through the facing layer for retention in an associated absorbent structure.

Because it is generally preferred that the facing layer of an absorbent article remain dry-feeling, even after use of the article, formation of facing layer material from polymers has been generally preferred. However, such polymeric material, by nature, is ordinarily hydrophobic. Accordingly, wetting agents in the form of surfactants are typically incorporated in or on the facing layer to promote transfer of liquid therethrough.

Internal wetting agents are sometimes blended, in pellet form, with the polymeric materials used to form facing layers, and thereby impart wettability in the resulting extrudate, whether in the form of fibers or apertured films. One such wetting agent consists of a fatty substance (glycerol and/or sorbitol) reacted with lauric acid, and is commercially available from Ciba Chemical under the name of "Atmer." The resultant surfactant product is then compounded with a polyolefin resin in a predetermined concentration. Heretofore, the common practice for compounding these wetting agents is to blend the maximum amount of surfactant in with a minimum amount of a carrier resin. Typically, the maximum fatty substance concentration used for this application has ranged from 15% to 17%, by weight, of the resultant compound.

Experience has shown that under certain conditions, use of additives such as described above can result in the formation of defects in the polymeric materials being formed, such as fiber breaks in spun-melt processes and holes in cast film. These defects are believed to result from the heterogeneous distribution of the fatty substance additives. Because such defects can preclude formation of commercially acceptable fabrics and films, the present invention is directed to an improved internal wetting agent that desirably acts to significantly abate the creation of such defects in polymeric fabrics and films.

SUMMARY OF THE INVENTION

An improved internal wetting agent embodying the principles of the present invention is contemplated for use by blending with polymeric material for formation of apertured films and/or polymeric fibrous webs. In distinction from previously known compositions, the present wetting agent consists essentially of between about 1% and 13%, by weight, of a wetting compound, and between about 0% and 44%, by weight, of titanium dioxide ($TiO_2$). The balance of the wetting agent comprises a polymeric carrier resin.

The present wetting agent desirably results in improved pellet surface characteristics, rheological properties, and performance in extrusion machinery. The resultant extudate is of higher quality, and results in less undispersed additives, which can undesirably interfere with efficient formation of high-quality nonwoven fabrics and cast polymeric films.

It is presently preferred that the wetting compound of the present wetting agent be provided in the range of 10% to 12.5%, by weight, with the preferred weight percentage of the titanium dioxide being from 38.5% to 40%. A presently preferred polymeric carrier resin is low-density polyethylene, with a current embodiment of the present invention comprising 12.5% of the wetting agent (liquid surfactant), 40% titanium dioxide, and 47.5% low-density polyethylene.

BRIEF DESCRIPTION OF THE DRAWINGS

FIG. 1 shows a schematic diagram of a diaper construction utilizing a topsheet formed in accordance with the present invention.

DETAILED DESCRIPTION

While the present invention is susceptible of embodiment in various forms, there is herein described a presently preferred embodiment, with the understanding that the present disclosure is to be considered as an exemplification of the invention, and is not intended to limit the invention to the specific embodiments disclosed herein.

In accordance with the present invention, an improved internal wetting agent is provided for blending with polymeric material, with the formation of apertured films and/or polymeric fibrous webs contemplated. Films and/or nonwoven fabrics of this nature are suited for use in disposable absorbent articles, particularly for the so-called top sheet or facing layer, which contacts the wearer during use. Because these polymeric materials from which these types of facing layers are made are typically hydrophobic, the provision of an internal wetting agent facilitates the passage of liquid through the facing layer into an associated absorbent structure.

Technologies capable of employing the internal wetting agent thermoplastic resin of the present invention include those which form continuous filament nonwoven fabrics and extruded films, as well as staple fiber nonwoven fabrics and continuous filament or staple fiber woven textiles.

In general, continuous filament nonwoven fabric formation involves the practice of the spunbond process. A spunbond process involves supplying a molten polymer, which is then extruded under pressure through a large number of orifices in a plate known as a spinneret or die. The resulting continuous filaments are quenched and drawn by any of a number of methods, such as slot draw systems, attenuator guns, or Godet rolls. The continuous filaments are collected as a loose web upon a moving foraminous surface, such as a wire mesh conveyor belt. When more than one spinneret is used in line for the purpose of forming a multi-layered fabric, the subsequent webs is collected upon the uppermost surface of the previously formed web. The web is then at least temporarily consolidated, usually by means involving heat and pressure, such as by thermal point bonding. Using this means, the web or layers of webs are passed between two hot metal rolls, one of which has an embossed pattern to impart and achieve the desired degree of point bonding, usually on the order of 10 to 40 percent of the overall surface area being so bonded.

The formation of finite thickness films from thermoplastic polymers is a well-known practice. Thermoplastic polymer films can be formed by either dispersion of a quantity of molten polymer into a mold having the dimensions of the desired end product, known as a cast film, or by continuously forcing the molten polymer through a die, known as an extruded film. Extruded thermoplastic polymer films can either be formed such that the film is cooled then wound as a completed product, or dispensed directly onto a substrate material to form a composite material having performance of both the substrate and the film layers. Examples of suitable substrate materials include other films, polymeric or metallic sheet stock and woven or nonwoven fabrics.

The application of the extruded film directly onto a substrate material imparts the substrate material with enhanced physical properties. It is known in the art that the application of a thermoplastic polymer film having suitable wettability and porosity onto a nonwoven fabric results in a composite material having significant wicking properties and is suitable for disposable hygiene garment manufacture.

Extruded films utilizing the composition of the present invention can be formed in accordance with the following representative direct extrusion film process. Blending and dosing storage comprising at least two hopper loaders, one for thermoplastic polymer chip and one for pelletized internal wetting agent in thermoplastic carrier resin, feed into two variable speed augers. The variable speed augers transfer predetermined amounts of polymer chip and additive pellet into a mixing hopper. The mixing hopper contains a mixing propeller to further the homogeneity of the mixture. Basic volumetric systems such as that described are a minimum requirement for accurately blending the internal wetting agent into the thermoplastic polymer. The polymer chip and additive pellet blend feeds into a multi-zone extruder. Upon mixing and extrusion from multi-zone extruder, the polymer compound is conveyed via heated polymer piping through screen changer, wherein breaker plates having different screen meshes are employed to retain solid or semi-molten polymer chips and other macroscopic debris. The mixed polymer is then fed into a melt pump, and then to a combining block. The combining block allows for multiple film layers to be extruded, the film layers being of either the same composition or fed from different systems as described above. The combining block is connected to an extrusion die, which is positioned in an overhead orientation such that molten film extrusion is deposited at a nip between a nip roll and a cast roll.

When a substrate material is to receive a film layer extrusion, a substrate material source is provided in roll form to a tension-controlled unwinder. The base layer is unwound and moves over the nip roll. The molten film extrusion from the extrusion die is deposited onto the substrate material at the nip point between the nip roll and the cast roll. The newly formed base layer and film composite is then removed from the cast roll by a stripper roll and wound onto a new roll.

Reticulated films, such as those of patent numbers U.S. Pat. No. 4,381,326 and U.S. Pat. No. 4,329,309, are representative of macroporous films. Such macroporous films, which are typically employed as the topsheet or facing layer of a disposable feminine hygiene product, come in direct contact with the body and benefit significantly from improved formation and wettability as embodied by the present invention.

During development of the present invention, standard commercial concentrate pellets, with 15.3% liquid addition, were found to form deleterious holes at a rejection rate of about 16% or greater in a film manufacturing line producing hydrophilic apertured film for use as a top sheet in feminine napkins. It was also found that extending the blend time by lowering throughput at the 15.3% liquid surfactant additional level provided no perceptible improvement in rejection rate. A sample of concentrate pellets at 12.5% and at 10% liquid surfactant addition were found to significantly reduce the rate of holes in the film being formed and reduce the rate of material rejection.

The improved internal wetting agent embodying the principles of the present invention consists essentially of between about 1% and 13%, by weight, of a wetting compound, in the preferred embodiment, the wetting compound being selected from derivatized fatty acids, and specifically under the brand of additives, and between about 0% and 44% titanium dioxide ($TiO_2$), by weight, with the balance of the wetting agent comprising a polymeric carrier resin. Preferably, the wetting compound is in the range of about 10% to 12.5%, by weight, with the titanium dioxide in the range of 38.5% to 40%, by weight. Use of low-density polyethylene as the polymeric carrier is presently preferred. Typically, the carrier resin is selected for use with a similar family of resins, such as use of low-density polyethylene with polyolefin polymeric material for film and/or fabric formation. Typically, the wetting agent is blended with the polymeric material used for film and/or fabric formation such that the final concentration of the wetting compound is in a broad range of about 0.2% to 3.0%, by weight, with a more preferred range of 0.2% to 1.8%, by weight.

In a presently preferred form, the wetting agent concentrate pellet was formulated with 12.5%, by weight, liquid surfactant, 40%, by weight, titanium dioxide, and 47.5%, by weight, low density polyethylene, as a carrier resin. Use of the concentrate pellet with polymeric material to achieve the above-described weight percentages was found to render the resultant apertured film hydrophilic. This desirably provides the film with the ability to wick and transfer bodily fluids. The pellet concentrate exhibits low surface moisture (less than 0.45%) when tested in an Arizona Max 2000 moisture analyzer at 1801 C. The concentrate pellet also exhibits high apparent shear viscosity (greater than 20 Pa-s) at low apparent shear rates (less than 10 sec.$^{-1}$) when tested in a capillary rheometer using a 5:1 Z454C 1 mm orifice die. The following Table shows hole reduction achieved due to lower surfactant level in the Atmer composition.

| Asset | Atmer Used | Total Slits | Scrap Slits For Holes | Waste From Holes |
|---|---|---|---|---|
| Line 2 | 15.3% Concentrate | 3039 | 499 | 16.4% |
|  | 10% Concentrate | 2267 | 163 | 7.2% |
| Line 3 | 15.3% Concentrate | 3394 | 1196 | 35.2% |
|  | 12.5% Concentrate | 1650 | 202 | 12.2% |

The current invention is intended for use in cast apertured films that use a melt-extrusion process. The concentrate can also be used in spun-melt fiber making processes if a similar carrier resin is used.

A number of end-use articles can be benefit from the inclusion or substitution of a pre-existing wettable layer with the wettable film and fabrics of the present invention, including, but not limited to, hygiene absorbent articles, such as diapers and catamenial products, and medical/industrial protective articles.

Disposable waste-containment garments are generally described in U.S. Pat. No. 4,573,986, U.S. Pat. No. 5,843,056, and U.S. Pat. No. 6,198,018, which are incorporated herein by reference.

An absorbent article incorporating an improved internal wetting agent of the present invention is represented by the topsheet 24 of the unitary disposable absorbent article, diaper 20, shown in FIG. 1. As used herein, the term "diaper" refers to an absorbent article generally worn by infants and incontinent persons that is worn about the lower torso of the wearer. It should be understood, however, that the present invention is also applicable to other absorbent articles such as incontinence briefs, incontinence undergarments, diaper holders and liners, feminine hygiene garments, training pants, pull-on garments, and the like.

FIG. 1 is a plan view of a diaper 20 in an uncontracted state (i.e., with elastic induced contraction pulled out) with portions of the structure being cut-away to more clearly show the construction of the diaper 20. As shown in FIG. 1, the diaper 20 preferably comprises a containment assembly 22 comprising a liquid pervious topsheet 24; a liquid impervious backsheet 26 joined to the topsheet; and an absorbent core 28 positioned between the topsheet 24 and the backsheet 26. The absorbent core 28 has a pair of opposing longitudinal edges, an inner surface and an outer surface. The diaper can further comprise elastic leg features 32; elastic waist features 34; and a fastening system 36 which preferably comprises a pair of securement members 37 and a landing member 38.

Catamenial products, such as feminine hygiene pads, are of the same general construction as the aforementioned diaper structure. Again, a topsheet and a backsheet are affixed about a central absorbent core. The overall design of the catamenial product is altered to best conform to the human shape and for absorbing human exudates. Representative prior art to such article fabrication include U.S. Pat. No. 4,029,101, U.S. Pat. No. 4,184,498, U.S. Pat. No 4,195,634, and U.S. Pat. No. 4,886,513, which are incorporated herein by reference.

From the foregoing, it will be observed that numerous modifications and variations can be affected without departing from the true spirit and scope of the novel concept of the present invention. It is to be understood that no limitation with respect to the specific embodiments illustrated herein is intended or should be inferred. The disclosure is intended to cover, by the appended claims, all such modifications as fall within the scope of the claims

What is claimed is:

1. A film comprising a continuously extruded sheet containing a polyolefin polymeric material and a wetting a agent provided in pellet form, wherein said wetting agent consists essentially of about 10% to 13% by weight of a wetting compound consisting of glycerol reacted with lauric acid, and between about 38% to 44% by weight of titanium dioxide ($TiO_2$), and the balance of said wetting agent is a low density polyethylene carrier resin with which said wetting compound and said titanium dioxide are blended, and the film contains 0.2% to 3.0% by weight of said wetting compound.

2. A film according to claim 1, wherein:
said titanium dioxide is provided in a range of about 38.5% to 40% by weight.

3. A film according to claim 2, wherein:
the film contains about 0.2% to 1.8% by weight of said wetting compound.

4. A film comprising a continuously extruded sheet containing a polyolefin polymeric material and a wetting agent provided in pellet form, wherein said wetting agent consists essentially of about 12.5% by weight of a wetting compound consisting of glycerol reacted with lauric acid, about 40% titanium dioxide ($TiO_2$), by weight, and about 47.5% by weight of low density polyethylene as a carrier resin, and the film contains about 0.2% to 1.8% by weight of said wetting compound.

\* \* \* \* \*